US006210947B1

(12) United States Patent
Dobson

(10) Patent No.: US 6,210,947 B1
(45) Date of Patent: Apr. 3, 2001

(54) ISOLATION AND SCREENING OF SUBCUTICULAR BRITTLESTAR BACTERIA FOR ANTIMICROBIAL COMPOUNDS PRODUCTION

(75) Inventor: William E. Dobson, Boone, NC (US)

(73) Assignee: Appalachain State University, Boone, NC (US)

( * ) Notice: Subject to any disclaimer, the term of this patent is extended or adjusted under 35 U.S.C. 154(b) by 0 days.

(21) Appl. No.: 09/061,556

(22) Filed: Apr. 16, 1998

(51) Int. Cl.$^7$ .............................. C12N 1/20; C12N 1/00; A01N 63/00
(52) U.S. Cl. ...................... 435/252.1; 435/909; 424/93.4
(58) Field of Search ................................. 435/909, 252.1; 424/93.4

(56) References Cited

U.S. PATENT DOCUMENTS

| 5,063,055 | * | 11/1991 | Burges et al. | 424/93 |
| 5,262,399 | * | 11/1993 | Hickle et al. | 514/12 |
| 5,695,552 | * | 12/1997 | Taylor | 106/15.05 |

OTHER PUBLICATIONS

Dobson et al. American Zoologist, 1997, vol. 37, No. 5, pp. 131A. Meeting Info.: Annual Meeting of the Society for Integrative and Comparative Biology, Boston, USA Jan. 3–7, 1998 Society for Integrative and Comparative Biology.*

Strahl et al. Abastracts of the General Meeting of the American Society for Microbiology, 1997, vol. 97, pp. 391. Meeting Info.: 97th General Meeting of the American Society for Microbiology, Miami Beach, Florida, USA, May 4–8, 1997.*

Lesser et al. Applied and Environmental Microbiology. Aug. 1990, vol. 56, No. 8, pp. 2436–2440.*

Bergey's Manual of Determinative Bacteriology. Ninth Edition, 1994, pp. 192–194, 260–274.*

Kelly et al. In: Echinoder Research 1991, Proceedings of the Third European Conference on Echinoderms, Lecce, Italy, Sep. 9–12, 1991. Edited by Scalera–Liaci et al., Rotterdam, 1992., pp. 225–228.*

Choudhury et al. Fems Microbiology Letters, 1994, 115, pp. 329–334.*

McKenzie et al. Marine Biology, 1994, 120, pp. 65–80.*

Kelly et al. Marine Biology, 1995, 123, pp. 741–756.*

* cited by examiner

Primary Examiner—Irene Marx
Assistant Examiner—Vera Afremova
(74) Attorney, Agent, or Firm—Jenkins & Wilson, P.A.

(57) ABSTRACT

A biologically pure culture comprising a subcuticular bacteria isolated from *A. gracillima* and having bacillus morphology and antimicrobial activity is described. A sample has been deposited at American Type Tissue Culture (ATCC) on Apr. 14, 1998 under accession numbers 202111, 202112, or 202113. Mutants or derivatives thereof having the same antimicrobial activity as the culture are also described. Antimicrobial compositions including the biologically pure culture and methods of inhibiting the growth utilizing the biologically pure culture are also described. Finally, an antibiotic or antibiotic fraction derivable from the bacteria is also disclosed.

8 Claims, 6 Drawing Sheets

Table 1

| | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|
| E. aerogenes | C | nd | nd | | | | | | | | | | | | | | | | |
| C. diphtheriae | C | B | C | | B | B | B | B C | | B | | B C | B | B | B | B | B | B C | B C |
| M. luteus | | nd | nd B | C | B | B | | C | | B | | B | B | | B | B | | | C |
| P. vulgaris | B | B | nd B | C C | B | | B C | B C | | B | | B C | B | B | B B | B | B C | C | B C |
| B. catarrhalis | | B | nd B | B C | B B | C | B C | B | B C | B | B C | B C | B | B | B C | A C | B C | C | B C |
| K. pneumoniae | C | B | nd B | | B | | B | B | | B | B | B | B | B | B | B | B | | B |
| S. ureae | | | nd B | | | C | B | B C | | | B B | B | B | C | | B | | | B C |
| S. aureus | C | B | nd B | | | C | | | | | B C | | B | | | C | | | B C |
| B. subtilis | C | | nd B | | B | B | B | | | B | B B | C | B | B | | C | B | | C |
| S. typhimurium | C | C | nd | C | | B | B | B | C | B | | B B C | B C | B | B | C | | C | B |
| B. anthracis | | B | nd | | | | | | | B C | B | B B C | B | | | A | B C | C | B C |
| E. coli | B | C | nd | B | B B | C | | B | | C | B C | B C | B C | B | B | A C | B | | B C |
| B. megaterium | C | nd C | nd | nd B | nd B | nd B | nd B | nd B | nd | nd | nd | nd | nd B | nd B | nd | nd | nd | nd | |
| M. smegmatis | | C | nd | C | B B | C | C | B C | | | C | B C | B | B | C | B | B B | | B C |
| P. aeruginosa | | C C | nd | C C | B C | | C | C | | C | | | | C | C | | | C | B |
| V. parahemolyticus | nd | nd | nd | nd | nd | nd | nd | nd | nd | nd | nd | nd | nd | nd | nd | nd | nd | nd | nd |
| S. marcescens | nd nd | nd C | nd nd | nd C | nd C | nd C | nd C | nd C | nd | nd | nd C | nd | nd | nd | nd C | nd | nd | nd B | nd B |
| S. mutans | nd nd | nd | nd nd | nd | nd | nd | nd | nd | nd | nd | nd | nd B | nd B | nd | nd | nd | nd | nd | nd |
| E. faecalis | nd nd | nd | nd nd nd | nd | nd | nd | nd C | nd C | nd | nd | nd | nd C | nd C | nd | nd | nd C | nd C | nd C | nd B |
| P. flurescens | nd nd | nd | nd | nd | nd | nd | nd | nd | nd | nd | nd | nd | nd | nd | nd | nd | nd | nd | nd |
| Y. enterocolitica | nd nd | nd | nd | nd | nd | nd | nd | nd | nd | nd | nd | nd | nd | nd | nd | nd | nd | nd | nd C |

FIG. 3-1

Table 1 (continued)

| | 31 | 32 | 33 | 34 | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|---|---|---|
| E. aerogenes | | B | | B | B C | | A B | B C | B C B | B | B C | B | B | | | | B C | | |
| C. diphtheriae | B | B | B C | B | B C | | A B | B C | B C | B | B C | B | B B | B | B | | B C | | C |
| M. luteus | | B B C | B | B B | B B | | A B B | B | B | | | | | | | B B B | B | |
| P. vulgaris | B B | B B | | B | B C | A | A B | B C | B C | B C | B C | B | B C B C | B C | B | B B B | B C | | |
| K. pneumoniae | | B C | | | | | A C | B B | B C | B | | | | | | | | | |
| S. ureae | C | | C B | B B B | | | A A | C B | C | B | | | C | | C | B C | B C | C C | C |
| S. aureus | B | B | B B | B C B | B C | B | A A | | C | B | C | | B | B | B | B | B C | C | C |
| B. subtilis | C | B | B B | B B | | C | B A | B | B | | | | B B | B B | | B | B B B | B | C |
| S. typhimurium | C C | B C | B B | B B | | | B B | B | B C B | B B | B B | | B B | | | B | B C | C | C |
| B. anthracis | B | B B | B B | B C | B | | A B | | C B | B | B C | | B C | B C | | B | B C | B | C |
| E. coli | B | B | B C | B C | B C | | A B | B | nd | nd | B C | | B C B | C | B | B | C nd B | C | C |
| B. megaterium | B nd | nd B | nd | nd | nd | nd B | nd | nd B | nd B nd | nd | nd | nd B | nd | nd | nd B | nd B | nd B | nd | nd |
| M. smegmatis | C | C B | C | B B | B C | C | C | B | B | | B | C | C B | C | B | C | B C | C | C |
| P. aeruginosa | C | C | C | C | C | C | C | C | C | C | C | C | C | C | | | | C | C |
| V. parahemolyticus | nd B | nd | nd | nd B | nd | nd B | nd | nd B | nd B | nd | nd | nd | nd | nd | nd | nd | nd | nd | nd |
| S. marcescens | nd | nd C | nd C | nd C | nd C | nd C | nd | nd C | nd C | nd C | nd C | nd | nd C | nd C | nd | nd C | nd C | nd C | nd C |
| S. mutans | nd B | nd B | nd | nd | nd C | nd C | nd A | nd C | nd C | nd | nd | nd | nd B | nd | nd | nd | nd C | nd C | nd |
| E. faecalis | nd C | nd C | nd | nd B | nd B | nd B | nd B | nd | nd B | nd B | nd B | nd | nd C | nd | nd | nd | nd | nd | nd |
| P. flurescens | nd C | nd | nd | nd | nd | nd C | nd B | nd | nd C | nd | nd | nd | nd C | nd | nd | nd | nd | nd | nd |
| Y. enterocolitica | nd C | nd C | nd | nd B | nd | nd C | nd B | nd | nd | nd B | nd | nd | nd B | nd B | nd B | nd C | nd B | nd B | nd |

FIG. 3-2

Table 1 (continued)

| | 50 | 51 | 52 | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|
| E. aerogenes | | | | B C | C | | | C | | | | | | | | | | | | C | C |
| C. diphteriae | B | B C | B | B B | B | | | C C | C | | A | B | B | B | C | C | C | C | C | C | B C |
| M. luteus | | B | B A | B B | B | | | C | | | B | C B | | | C C | C | | | C C | C B | C C |
| P. vulgaris | B C | B | | B | C A | A B | | B A | | A C | A | A B A | A | A | B | B | B | B | B A | A B | A |
| B. catarrhalis | B C | B | A B | B B | A | C | | C C | | | B C | B C B | B C | B B | B | | C | C C | C | C C | C |
| K. pneumoniae | B | B | B | B B | | | | C | | | C | B | B | B | C | | C | C | B C | B | C |
| S. ureae | B C | B | A | A B C | C | C | | C | | | C | | C | B | | C | A | C B | | C | C |
| S. aureus | B | B C | A | A B | C | C | | C | B | C | | | C | C | | | | C C | C | C | C |
| B. subtilis | B | | A | A B | C | C | | | | | C | C | C | C | | | | C | | | C |
| S. typhimurium | B C | B B | A C | A C A | A C | A | | C | | B | B C | B C B | B | A | | C | C B | | C | C C | C C |
| B. anthracis | B C | B C | A B | A B | B A | | | A C C | B | | B C | B | B | A B | B | C | C | | C | C | C |
| E. coli | B C | B | B | A B | B C | | | C C | B C | | B C | C | B | B | B | C | | | B C | C | B C |
| B. megaterium | nd | nd A | nd A | nd | nd C | nd | nd | nd | nd | nd | nd | nd | nd | nd | nd C | nd | nd C | nd C | nd | | |
| M. smegmatis | B B | B C | A | A | C | C | | B B | | | | C | C | nd | B A | B A | B C | A C | A C | | |
| P. aeruginosa | B C | B C | A | C | C | | | C | C | B C | | | C | C | | C | C | C | A B | A B | C |
| V. parahemolyticus | B | B | B | nd | nd | nd | nd | nd | nd B | nd | nd | nd | nd B | nd B | nd | nd | nd C | nd C | nd C | C C | B C |
| S. marcescens | nd C | nd C | nd A | nd C | nd C | nd C | nd | nd C | nd C | nd C | nd C | nd C | nd C | nd C | nd C | nd | nd C | nd C | nd | nd C | nd C |
| S. mutans | nd | nd | nd B | nd B | nd C | nd C | nd | nd C | nd C | nd | nd | nd B | nd C | nd | nd | nd | nd A | nd A | nd A | nd | nd |
| E. faecalis | nd | nd | nd A | nd A | nd A | nd A | nd | nd B | nd B | nd C | nd C | nd B | nd | nd B | nd | nd | nd C | nd C | nd C | nd C | nd C |
| P. flurescens | nd | nd | nd B | nd B | nd C | nd C | nd | nd C | nd C | nd C | nd C | nd C | nd | nd C | nd | nd | nd C | nd C | nd B | nd B | nd B |
| Y. enterocolitica | nd | nd | nd B | nd A | nd | nd | nd C | nd C | nd C | nd | nd | nd C | nd | nd | nd | nd | nd C | nd C | nd C | nd C | nd B |

FIG. 3-3

ISOLATION AND SCREENING OF SUBCUTICULAR BRITTLESTAR BACTERIA FOR ANTIMICROBIAL COMPOUNDS PRODUCTION

TECHNICAL FIELD

The present invention relates to antimicrobial compounds produced by subcuticular bacteria of a brittlestar, to methods of producing such antimicrobial compounds, and to biologically pure strains of subcuticular bacteria of a brittlestar producing such compounds.

| Table of Abbreviations and Symbols | |
|---|---|
| A. gracillima | Amphipholis gracillima, a species of brittlestar |
| ATCC | American Type Culture Collection |
| B. anthracis | Bacillus anthracis |
| B. megaterium | Bacillus megaterium |
| B. subtilis | Bacillus subtilis |
| B. catarrhalis | Branhamella catarrhalis |
| BE | brittlestar extract |
| C. diphtheriae | Corynebacterium diphtheriae |
| DNA | deoxyribonucleic acid |
| E. aerogenes | Enterobacter aerogenes |
| E. coli k-12 | Escherichia coli k-12 |
| HPLC | high performance liquid chromatography |
| K. pneumoniae | Klebsiella pneumoniae |
| M. luteus | Micrococcus luteus |
| M. smegmatis | Mycobacterium smegmatis |
| ‰ | standard symbol indicating salinity by weight |
| PCR | polymerase chain reaction |
| P. vulgaris | Proteus vulgaris |
| P. aeruginosa | Pseudomonas aeruginosa |
| pSCB | putative subcuticular bacteria |
| RFLP | restriction fragment length polymorphism |
| RNA | ribonucleic acid |
| rRNA | ribosomal ribonucleic acid |
| SCB | subcuticular bacteria |
| S. typhimurium | Salmonella typhimurium |
| S. ureae | Sporosarcina ureae |
| S. aureus | Staphylococcus aureus |
| TBE | Tris-borate-EDTA |
| TEM | Transmission electron microscope |
| UV | ultraviolet |
| V. parahemolyticus | Vibrio parahemolyticus |

BACKGROUND ART

Associations between marine invertebrates and endosymbiotic bacteria are increasingly recognized as widespread and of biological importance (McKenzie and Kelly 1994). Examples of marine invertebrates utilizing symbiotic bacteria include sponges, annelids, bivalve molluscs, cephalopods, and echinoderms (Kelly et al. 1995). Of the five extant classes of echinoderms, all are known to harbor symbiotic bacteria directly below the cuticle, lying in or within the folds of the dermal lamallae (McKenzie and Kelly 1994; Kelly et al. 1995). Holland and Nealson (1978) first described these bacteria, known as subcuticular bacteria (SCB). Little is known of the biology and role of SCB relative to their hosts, but chemoautotrophic symbionts are found in sea-urchin guts, and some feather stars (criniods) are known to have bacteria enclosed in their pinnules (McKenzie and Kelly 1994).

Many morphological studies of SCB have been done. Transmission electron microscope (TEM) observations of SCB revealed that they are Gram-negative bacilli (McKenzie and Kelly 1994). The SCB found in *Amphipholis (Microphiopholis) gracillima* (Ophiuroidea) (hereinafter "*A. gracillima*") were described by McKenzie and Kelly (1994) as single straight rods, with membrane-bound vacuoles. All SCB examined by McKenzie and Kelly (1994) had simple, thin capsules. None of the bacteria observed in *A. gracillima* tissues exhibited evidence for flagella or pili, nor showed any type of mobility (McKenzie and Kelly 1994; Kelly and McKenzie 1995).

SCB could play a role in defense against bacterial infestation during tissue regeneration. Since brittlestars exhibit the ability to autotomize and then regenerate body parts, brittlestars are candidates for pathogenic microbial colonization (Bryan et al. 1994). Bryan et al. (1994) proposed that antimicrobial compounds, produced by echinoderms, would help prevent infection by pathogenic bacteria and thus prevent surface fouling of epithelial tissue that can deplete respiratory capacity, impede elimination of waste products, and reduce tissue elasticity. Lubchenco et al. (1991) suggested SCB and echinoderms may have evolved a mutualistic relationship that provides for protection against colonization of other bacterial species.

McKenzie and Kelly (1994) showed that regenerating tissue, such as damaged ophiuroid arm tips, are quickly colonized by SCB. When the arms of *Amphipholis gracillima* were surgically removed, SCB colonized the wound closure within 1 hour and almost completely covered the regenerating stump within 24 hours (Dobson 1988). Due to this rapid proliferation, SCB may limit colonization of pathogenic bacteria due to competitive exclusion, production of a compound which exhibits antimicrobial activity, or both.

Despite the aforementioned study of SCB in the prior art, the isolation of putative SCB from intact and regenerating brittlestars and subsequent characterization of those bacteria for ability to chemically inhibit the growth of pathogenic bacteria in culture has not been described. Isolation and characterization of putative SCB are highly desirable given the need to determine whether such bacteria produce antimicrobial compounds and given the broad utility of any such compounds produced by the bacteria as potential antimicrobials.

SUMMARY AND OBJECTS OF THE INVENTION

In accordance with the present invention there are provided biologically pure cultures of subcuticular bacteria isolated from *A. gracillima* and having bacillus morphology, samples of which has been deposited at American Type Tissue Culture (ATCC) on Apr. 14, 1998 under accession numbers 202111, 202112, and 202113, or a mutant or a derivative thereof having the same antimicrobial activity as the culture.

In accordance with the present invention there is also provided a biologically pure culture of a subcuticular bacteria isolated from *A. gracillima* and having bacillus morphology, further characterized as a monoculture selected from monocultures BE 12 through BE 70 as set forth in Table 1 of FIG. 3 and having the anti-microbial activity thereof, or a mutant or a derivative thereof having the same antimicrobial activity as the monoculture. Preferably, the biologically pure culture is further characterized as a monoculture selected from the group consisting of monocultures BE 37, BE 52 and BE 59 as set forth in Table 1 of FIG. 3 and in Examples 1 through 3, displaying Hae III restriction fragment length polymorphism (RFLP) banding patterns of polymerase chain reaction (PCR)-amplified DNA from the 16S rRNA gene as shown in FIG. 4, and having the anti-microbial activity thereof, or a mutant or a derivative thereof having the same antimicrobial activity as the respective monoculture.

In accordance with the present invention, there is also provided an antimicrobial composition comprising the biologically pure culture as described above, or a mutant or a derivative of any of such culture, the mutant or the derivative having the same antimicrobial activity as the culture, or antimicrobial material isolated from any of such cultures, together with a carrier or diluent therefor. Further, a method for inhibiting the growth of a microbe comprising the step of contacting said microbe with an inhibiting amount of the antimicrobial composition of the present invention is also provided.

In accordance with the present invention there is also provided an antibiotic or antibiotic fraction derivable from subcuticular bacteria isolated from *A. gracillima*, wherein the isolated bacteria have bacillus morphology. The antibiotic or antibiotic fraction is characterized by (a) antibiotic activity against Gram-positive bacteria, Gram-negative bacteria and combinations thereof; (b) antimicrobial activity over a pH range of about 6.4 to about 8.4; (c) solubility in water and ethanol; (d) insolubility in toluene and chloroform; and (e) precipitability from an aqueous solution using either toluene or chloroform. A process for obtaining such an antibiotic or antibiotic fraction is also provided.

Therefore, it is an object of the present invention to isolate and to characterize putative subcuticular bacteria from *A. gracillima*.

It is another object of the present invention to isolate and to characterize compounds produced by such bacteria for use as antimicrobials.

It is a further object of the present invention to provide a biologically pure culture of a subcuticular bacteria isolated from *A. gracillima*.

It is yet a further object of the present invention to provide an antibiotic or antibiotic fraction derivable from subcuticular bacteria isolated from *A. gracillima*.

It is still a further object of the present invention to provide methods for inhibiting microbial growth using the biologically pure cultures and antibiotic or antibiotic fraction of the present invention.

Some of the objects of the invention having been stated hereinabove, other objects will become evident as the description proceeds, when taken in connection with the Laboratory Examples and the accompanying drawings as best described hereinbelow.

BRIEF DESCRIPTION OF THE DRAWINGS

FIG. 3 shows Table 1, which presents rapid-streak testing of BE isolates for antimicrobial activity against several common pathogenic bacteria at 35‰ and 10‰ salinities. All unshaded columns are results from 35‰ sensitivity tests whereas all shaded columns are results for the 10‰ sensitivity tests. BE numbers for each isolate are listed across the top of Table 1. 'A' represents complete inhibition produced by the BE isolate; 'B' represents moderate inhibition; and 'C' means partial inhibition. 'nd' indicates that the particular test bacterium was not tested at that salinity. Blank cells represent no inhibition or very slight inhibition. A description of inhibition levels is presented below. Note that *B. megaterium* was not tested at 10‰ due to procedural flaws.

DETAILED DESCRIPTION OF THE PREFERRED EMBODIMENT

Ophiuroid echinoderms (brittlestars) harbor bacteria, known as subcuticular bacteria (SCB), in their dermal tissues. It has been hypothesized that SCB are symbiotic, providing metabolites or other benefit to the echinoderm host in exchange for living space. Tests were conducted to isolate SCB from *Amphipholis gracillima* tissue and determine if they produce chemical antimicrobial compounds that help the brittlestar fend off bacterial infection during wound healing and regeneration after autotomy. As described below, fifty-nine bacilli isolates obtained from *Amphipholis gracillima* tissue exhibited some level of antimicrobial activity to one or more of 21 species of pathogenic bacteria. Thirty-nine of the isolate bacilli inhibited one or more of 20 pathogenic bacteria species under human physiologic conditions (10‰ salinity and 37° C. incubation temperature). These results indicate that brittlestars harbor several strains of SCB which provide their hosts with chemical defenses against adverse bacterial infection. The water-soluble inhibitory chemicals produced by the SCB also function as antimicrobial compounds against human pathogenic bacteria.

Biologically Pure Culture

Therefore, a biologically pure culture of a subcuticular bacteria isolated from *A. gracillima* and having bacillus morphology, a sample of which has been deposited at American Type Tissue Culture (ATCC) on Apr. 14, 1998 under accession numbers 202111, 202112, 202113, or a mutant or derivative thereof having the same antimicrobial activity as the culture is disclosed herein. The ATCC collection is accessible via the following address: ATCC American Type Culture Collection, 10801 University Boulevard, Manassas, Va. 20110-2209. All restrictions on the availability to the public of the deposited material will be irrevocably removed upon the granting of a patent.

Figure 4:
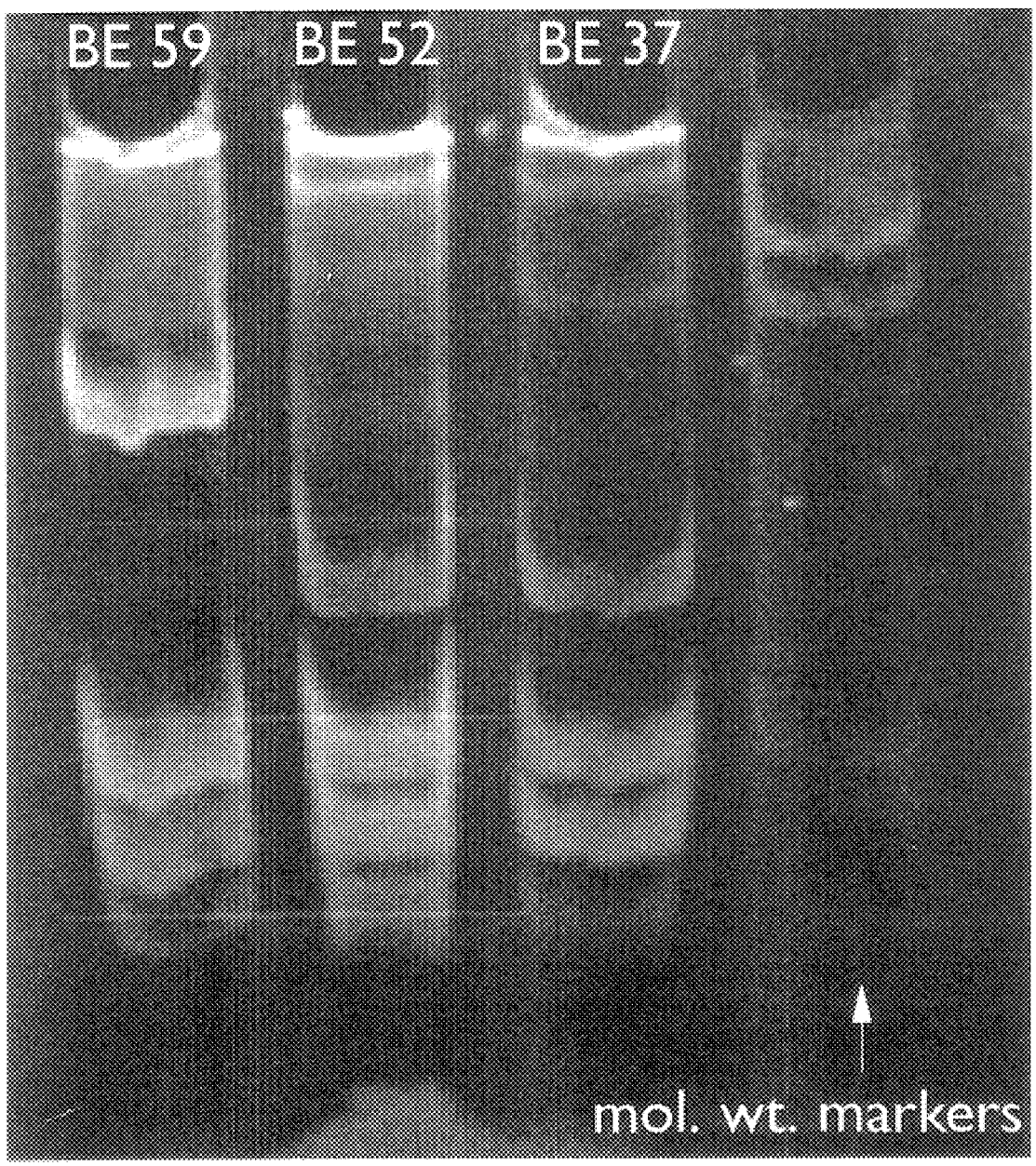
FIG. 4 depicts gel electrophoresis displaying Hae III restriction fragment length polymorphism (RFLP) banding patterns of polymerase chain reaction (PCR)-amplified DNA from the 16S rRNA gene of isolates BE 37, BE 52, and BE 59. Standard molecular weight markers are also displayed.

The present invention also provides a biologically pure culture of a subcuticular bacteria isolated from *A. gracillima* and having bacillus morphology, further characterized as a monoculture selected from monocultures BE 12 through BE 70 as set forth in Table 1 of FIG. 3 and having the anti-microbial activity thereof, or a mutant thereof having the same antimicrobial activity as the monoculture. The preferred biologically pure culture is further characterized as a monoculture selected from the group consisting of monocultures BE 37 (ATCC 202111), BE59 (ATCC 202112) and BE52 (ATCC 202113) as set forth in Table 1 of FIG. 3 and in Examples 1 through 3, displaying Hae III restriction fragment length polymorphism (RFLP) banding patterns of polymerase chain reaction (PCR)-amplified DNA from the 16S rRNA gene as shown in FIG. 4, and having the anti-microbial activity thereof, or a mutant thereof having the same antimicrobial activity as the monoculture.

Optionally, the biologically pure culture of the present invention, or equivalent mutants or derivatives thereof, is capable of producing an antimicrobial composition in a recoverable amount upon aerobic fermentation in an aqueous nutrient medium containing assimilable sources of carbon, nitrogen, and inorganic salts.

Antimicrobial Compositions and Methods

More suitably, the biologically pure culture is in a form suitable for use in control of microbial infection or microbial contamination. Indeed, an antimicrobial composition is also disclosed herein. The antimicrobial composition comprises the biologically pure culture as described above, or a mutant or a derivative of any of such culture, the mutant or derivative having the same antimicrobial activity as the culture, or antimicrobial material isolated from any of such cultures, together with a carrier or diluent therefor. The antimicrobial composition is preferably in a form suitable for use in control of microbial infection or microbial contamination. Optionally, the antimicrobial composition can also include excipients, such as a gum or surfactant, suitable examples of which are well-known and thus would be apparent to one having ordinary skill in the art.

Further, a method for inhibiting the growth of a microbe comprising the step of contacting the microbe with an inhibiting amount of the antimicrobial composition of the present invention is also provided. Such a method has a wide range of applications, including the treatment of microbial infections in animals including humans, the treatment or prevention of microbial contamination of a water supply, and the treatment or protection of crops or other plants from microbial infection. Other examples would be apparent to one having ordinary skill in the art.

Antibiotic or Antibiotic Fraction

The present invention further provides an antibiotic or antibiotic fraction derivable from a subcuticular bacteria isolated from A. gracillima, wherein the isolated bacteria has bacillus morphology. The antibiotic or antibiotic fraction is characterized by (a) antibiotic activity against Gram-positive bacteria, Gram-negative bacteria and combinations thereof; (b) antimicrobial activity over a pH range of about 6.4 to about 8.4; (c) solubility in water and ethanol; (d) insolubility in toluene and chloroform; and (e) precipitability from an aqueous solution using either toluene or chloroform.

The antibiotic or antibiotic fraction of the present invention may be further described by the following characteristics: (a) a positive reaction to the following tests for the presence of protein: Pierce Commasse Plus Assay, Pierce Chemical Co., PO Box 117, Rockford, Ill., 61105, United States of America and (b) antibiotic activity at ambient temperature and at about 37° C.

A process for producing an antibiotic or antibiotic fraction having the following characteristics: (a) antibiotic activity against Gram-positive bacteria, Gram-negative bacteria, and combinations thereof; (b) antimicrobial activity over a pH range of about 6.4 to about 8.4; (c) solubility in water and ethanol; (d) insolubility in toluene and chloroform; and (e) precipitability from an aqueous solution using either toluene or chloroform, is also disclosed herein.

The process comprises culturing a microorganism capable of producing the antibiotic, and recovering the antibiotic from the culture.

Preferably, the microorganism is a subcuticular bacterium isolated from A. gracillima and having bacillus morphology, samples of which have been deposited at American Type Tissue Culture (ATCC) on Apr. 14, 1998 under accession numbers 202111, 202112, or 202113, or an antibiotic-producing derivative or mutant thereof.

The preferred microorganism may also be characterized as a subcuticular bacteria isolated from A. gracillima and having bacillus morphology, further characterized as a monoculture selected from monocultures BE 12 through BE 70 as set forth in Table 1 and having the anti-microbial activity thereof, or an antibiotic-producing derivative or mutant thereof. More preferably, the biologically pure culture is further characterized as a monoculture selected from the group consisting of monocultures BE 37 (ATCC 202111), BE59 (ATCC 202112) and BE52 (ATCC 202113) as set forth in Table 1 of FIG. 3 and in Examples 1 through 3, displaying Hae III restriction fragment length polymorphism (RFLP) banding patterns of polymerase chain reaction (PCR)-amplified DNA from the 16S rRNA gene as shown in FIG. 4, and having the anti-microbial activity thereof, or a mutant or a derivative thereof having the same antimicrobial activity as the monoculture.

The antibiotic of the present invention is produced upon fermentation of isolated subcuticular bacteria, such as those particularly described in Examples 1 through 3, or an active mutant or derivative thereof, in an aqueous nutrient medium containing assimilable sources of nitrogen and carbon under submerged aerobic conditions. By "active mutant or derivative thereof" it is meant a mutant or derivative of the bacteria which is capable of producing the antibiotic in recoverable quantity. Such mutants or derivatives can be prepared by standard techniques including irradiation, selection and chemical mutagenesis. Antibiotic producing mutants and derivatives can be readily selected by the techniques illustrated herein. Additionally, artificial variants and mutants of the bacteria can be obtained by treatment with various known mutagens, such as UV rays, X-rays, high frequency waves, radioactive rays, and chemicals such as nitrous acid, N-methyl-N'-nitro-N-nitrosoguanidine, and many others. Moreover, all natural and artificial variants and mutants which belong to the genus Vibrio and produce the antibiotic complex of the present invention are deemed to be equivalent to the strain ATCC 202111, 202112, or 202113 and are contemplated to be within the scope of this invention.

Additionally, as would be apparent to one having ordinary skill in the art, artificial variants, derivatives and mutants which are contemplated to be within the scope of the present invention can be produced using the conventional techniques of molecular biology. Such techniques include, for example, cloning the gene(s) associated with and/or responsible for antimicrobial synthesis by the BE isolates into a plasmid for transformation of a more easily grown bacterium (e.g. E. coli) and expression in such according to standard techniques, such as those described in Sambrook et al. (1989).

For producing the antibiotics, subcuticular bacteria isolated from A. gracillima and having bacillus morphology as described above, or an equivalent mutant or derivative thereof, are cultivated under submerged aerobic conditions in an aqueous nutrient medium containing assimilable sources of carbon, nitrogen and inorganic salts. The culture medium can be any one of a number of nutrient media usually employed in the fermentation art, however certain media are preferred. Thus, for instance, preferred carbon sources include those sugars, alcohols, amino acids and other acids presented in Table 5 below, and could further include starch, cellobiose, raffinose, fructose, dextrine, molasses and the like. Other useful carbon sources include peanut oil, corn oil, soybean oil, fish oil, and the like.

Preferred nitrogen sources are yeast extracts, amino acids (including but not limited to those presented in Table 5), casein hydrolysate, beef extract, soybean flour, peptones, and the like. Other useful nitrogen sources include oatmeal, peanut meal, soybean meal, soybean grits, cotton-seed meal, and the like.

Among the inorganic salts which can be incorporated in the culture media, there are the customary soluble salts capable of yielding sodium, potassium, iron, zinc, cobalt, magnesium, calcium, ammonium, chloride, carbonate, sulfate, nitrate, phosphate and the like ions. Trace elements such as nickel, selenite, molybdate, tungstate, and copper for the growth and development of organism should also be included in the culture medium. Such trace elements commonly occur as impurities in the other constituents of the medium in amounts sufficient to promote the growth requirements of the organism.

Additionally, a range of 0.001 to 0.1% by weight of ground-up, sterilized (by autoclaving) brittlestar is preferably included within the culture medium. Preferred salinity ranges from 0.1 to 3.5‰.

It is also preferred to add small amounts (e.g. 0.2 ml/l) of an antifoam agent such as polypropylene glycol or silicone derivatives to large scale fermentation media if foaming becomes a problem.

Ordinarily the antibiotic producing strain is pre-cultured in a shake flask. Then, the culture is used to inoculate jar fermentors for the production of substantial quantities of the antibiotic or antibiotic fraction. The medium used for the pre-culture can be the same as that employed for larger fermentations, but other media can also be employed.

Optionally, the fermentation may be carried out across a temperature range from about 20° C. to about 37° C., with a preferred temperature range of about 25° C. to about 32° C. A most preferred temperature is about 28° C. The fermentation may also be carried out at a pH ranging between about 6.4 and about 8.4. A more preferred pH range comprises about pH 7.8 to about pH 8.4. The fermentation may also be carried out for about 10 to about 100 hours, more preferably about 25 to about 75 hours, with a most preferred duration of about 48 hours, with agitation. As a customary procedure in aerobic submerged culture processes employing jar fermentors, sterile air is blown through the culture medium. For efficient growth of the organism, the volume of air preferably employed in the production tank is an amount sufficient to maintain a dissolved oxygen concentration greater than 20 percent.

During the fermentation, antibiotic production can be followed by testing samples of the broth for antibiotic activity. Organisms established herein to be sensitive to the present antibiotics are useful for this purpose. Especially useful assay organisms are *S. aureus, S. typhimurium, P. fluorescens*, and *M. luteus*. The bioassay is easily made by agar diffusion method on agar plates. Maximum antibiotic activity generally occurs at about 48 hours of incubation at the above outlined fermentation conditions.

Following this production under submerged aerobic fermentation conditions, the antibiotic can be recovered from the fermentation medium by methods used in the fermentation art, including, for example, extractions with solvents, counter-current extractions, precipitation by non-solvents, column chromatography, thin layer chromatography and the like, and can be further purified by techniques such as crystallization from solvents, liquid chromatography, high performance liquid chromatography (HPLC), reverse-phase HPLC, and the like.

The antibiotics produced during the fermentation of the antibiotic producing organisms are found in the culture broths. A preferred method for recovering the antibiotic is therefore by extraction of the filtered fermentation broths. Thus, after separating the cell mass by filtration, the antibiotic is recovered from the filtrate by extraction with a suitable solvent.

According to a preferred embodiment, a crude precipitate containing antimicrobial activity was prepared by adding an equal volume of toluene or chloroform to clarified culture medium from a 48-hour culture. After thoroughly shaking the mixture, the mixture was centrifuged to separate the aqueous and organic phases. The precipitate at the interface of the phases was removed and dried overnight. After resuspending the precipitate in a minimal volume of water or ethanol, a disk diffusion antimicrobial sensitivity assay was performed on Mueller-Hinton agar.

The obtained antibiotic can be further purified by known purification techniques, preferably using preparative thin layer chromatography or column chromatography. Absorbent materials such as alumina, silica gel, ion exchange resins such as those sold by Dow Chemical Co. under the registered trademark DOWEX®, cellulose, ion exchange resins and filtration media such as those sold by Pharmacia Fine Chemicals under the registered trademark SEPHADEX® and the like can be advantageously used.

For production of substantial quantities of the antibiotic, submerged aerobic fermentation in tanks is preferred. Small quantities of the antibiotic may be obtained by shake-flask culture. Because of the time lag in antibiotic production commonly associated with inoculation of large tanks with small amounts of the culture, it is preferable to use a vegetative inoculum that contains larger quantities of cells in an actively growing state. The vegetative inoculum is prepared by inoculating a small volume of culture medium with midexponential phase cells of the organism to obtain a fresh, actively growing culture of the organism. The vegetative inoculum is then transferred to a larger tank. The medium used for the growth of the vegetative inoculum can be the same as that used for larger fermentation, but other media can also be used.

Following its production under submerged aerobic fermentation conditions, the antibiotic previously described can be recovered from the fermentation medium by methods used in the fermentation art. The antibiotic activity produced during the fermentation occurs mainly in the broth. Maximum recovery of the antibiotic is accomplished, therefore, by a combination of methods, including filtration, extraction of the filtered broth, and absorption chromatography.

Alternatively, the culture solids, including medium constituents and cell mass, can be used without extraction or separation, but preferably after removal of water, as a source of the antibiotic. For example, after production of antibiotic activity, the culture medium can be dried by lyophilization and mixed directly into a composition for subsequent use, such as an antimicrobial composition.

In another aspect, after production of antibiotic activity in the culture medium and separation of the cell mass, the filtered broth can be lyophilized to give the antibiotic or antibiotic fraction in a form which can be used directly in a composition for subsequent use, such as an antimicrobial composition.

An antibiotic or antibiotic fraction obtainable by culturing the strain ATCC 202111, 202112, or 202113, or antibiotic or antibiotic fraction-producing mutants and derivatives thereof is therefore described. The strain is cultured under submerged aerobic conditions, in an aqueous nutrient medium containing assimilable sources of carbon, nitrogen and inorganic salts until substantial antibiotic or antibiotic fraction activity is imparted to the culture medium. The fermented medium is then filtered, and the antibiotic or antibiotic fraction is extracted from the filtrate and precipitated from the extract.

Compositions and Methods Utilizing Antibiotic

The antibiotic or antibiotic fraction of the present invention include salts thereof. The term "salts", as used herein, denotes acidic and/or basic salts, formed with inorganic and/or organic acids and bases. While pharmaceutically acceptable salts are preferred, particularly when employing the antibiotic or antibiotic fractions of the invention as medicaments, other salts find utility, for example, in processing these antibiotic or antibiotic fractions, or where non-medicament-type uses are contemplated.

It is preferred that the inventive antibiotic or antibiotic fractions have a degree of purity such that they are suitable for use as antibiotic agents. A particularly preferred embodiment of the instant invention provides the antibiotic, antibiotic fraction or a salt thereof in a substantially pure state. The substantially pure antibiotic or antibiotic fractions are preferably employed in the compositions and methods described following.

Hosts treatable according to the method of the present invention include plants and animals, particularly mammals such as dogs, cats and other domestic animals and, especially, humans. The dosage form and mode of administration, as well as the dosage amount, may be selected by the skilled artisan. The dosage amount will vary with the severity of the infection, and with the size and species of the host. Exemplary daily dosages for an adult human are those within the range of from about 2.5 mg to about 2,000 mg/day. Administration to a mammalian host, may, for example, be oral, parenteral, or topical. Administration to a plant host may be accomplished, for example, by application to seed, foliage or other plant part, or to the soil.

Compositions are also provided by the present invention which comprise the antibiotic or antibiotic fraction of the present invention, or a physiologically tolerated salt thereof in an amount effective for the treatment of infection by a microorganism, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to the skilled artisan. Treatment of simultaneous infections by more than one bacterium is, or course, contemplated.

The inventive antibiotic or antibiotic fractions may also be employed as antimicrobial agents useful in inhibiting the growth of microorganisms present on a surface or in a medium outside a living host. The present invention therefore provides a method for inhibiting the growth of at least one microorganism present on a surface or in a medium, comprising the step of contacting the surface or medium with the antibiotic or antibiotic fraction or a salt thereof in an amount effective for the inhibition. Thus, the inventive antibiotic or antibiotic fractions may be employed, for example, as disinfectants for a variety of solid and liquid media susceptible to microbial growth. Suitable amounts of the inventive antibiotic or antibiotic fractions may be determined by methods known to the skilled artisan. Compositions comprising the antibiotic or antibiotic fraction described herein, or a salt thereof, in an amount effective for inhibiting the growth of at least one bacterium, and a vehicle or diluent, are also provided by the present invention.

The present invention also relates to a method for inhibiting the growth of a microbe comprising the step of contacting the microbe with an inhibiting amount of the antibiotic or antibiotic fraction described above. Thus, a composition for the inhibition of the growth of a microbe comprising the antibiotic or antibiotic fraction describe above in an amount effective for the inhibition and a carrier or diluent is also provided.

The inventive antibiotic or antibiotic fractions are therefore useful as antimicrobial agents, useful in inhibiting the growth of microorganisms, particularly bacteria such as Gram-positive and Gram-negative bacteria, for example, the bacteria listed in Tables 1 through 4, including bacteria of the genera Escherichia, Klebsiella, Proteus, Serratia, Bacillus and Staphylococcus. Inhibition of the growth of a bacterium may be achieved by contacting the bacterium with a compound of the present invention in an amount effective therefor.

Thus, the antibiotic or antibiotic fractions of the present invention may be employed in utilities suitable for antimicrobial agents. The inventive antibiotic or antibiotic fractions may, for example, be used in treating a host infected with a bacterium, comprising the step of administering to the host the antibiotic or antibiotic fraction, or a physiologically tolerated salt thereof in an amount effective for the treatment. Treatment of such infections according to the instant invention includes both mitigation as well as elimination thereof.

An antibacterial composition comprising an antibacterial effective amount of the antibiotic or antibiotic fraction produced by the process described above and a pharmaceutically acceptable carrier is also provided. Additionally, a method for treating or preventing infection in an animal by a Gram positive pathogenic bacterium or a Gram negative pathogenic bacterium which comprises orally, parenterally or topically administering to the animal an antibacterial effective amount of such an antibacterial composition is also provided.

General fermentation, extraction and characterization techniques which are suitable for use in accordance with the present invention are well known in the art. See, for example, U.S. Pat. Nos. 4,247,542; 4,692,333; 4,694,069; 5,061,495; 5,344,647; 5,364,623; 5,470,827; 5,614,188; and 5,695,552, the contents of each of which are herein incorporated by reference, and which listing is not intended to be exhaustive.

LABORATORY EXAMPLES

Collection of Brittlestars

*Amphipholis gracillima* (hereinafter "*A. gracillima*") were collected from North Inlet Estuary, north of Georgetown, S.C., in late spring. Animals were transported to applicants' laboratory in Boone, N.C. in refrigerated portable aquaria containing natural sediment and natural seawater. In the laboratory, animals were transferred to 10 gallon aquaria containing natural seawater and substrate from the estuary. The brittlestars were maintained in these aquaria for the duration of the study.

Isolation and Cultivation of Putative Subcuticular Bacteria

Putative subcuticular bacteria (pSCB) were isolated from brittlestar tissue using four isolation regimens (FIG. 1): (1) whole intact *A. gracillima* were rinsed in two changes of sterile seawater, homogenized using a glass homogenizer, and the homogenate serially diluted and plated; (2) as in the first procedure above except the sterile seawater rinses were preceded by a 30 second rinse in 70% ethanol; (3) an arm was aseptically amputated, and after one hour the wound was swabbed with a sterile cotton-tipped applicator, followed by streaking the surface of a plate using the swab; (4) an arm was aseptically removed, and after one hour the wound stump tissue was dissected out and plated.

These four different methods were used to insure from the start that all possible sources of bacteria were exploited and differentiated. The first method was the standard procedure for extracting bacteria from tissue samples, after rinsing off external material to reduce the possibility of culturing external bacteria. The second method was an extension of the first, with the ethanol dip as an attempt to actively destroy any external bacteria. The third method was based on prior work which showed bacteria aggregated in post-autotomy wound sites within one hour after autotomy. The fourth method was same as the third method, but used actual wound site tissues in case the swabbing technique was not successful in transferring bacteria to the culture medium.

The growth medium used for isolation and maintenance of the pSCB was a modification of Zobel's medium (Zobel 1941). Natural seawater from the estuary was used in place of artificial sea salts and peptone and yeast extract were each added at 1 g/L of medium. The pH of the medium was maintained between 7.8 and 8.4. The cultures were incubated at 28° C. and examined daily for growth. Additionally, a range of 0.001% to 0.1% by weight of ground-up, sterilized (by autoclaving) brittlestar was included within the culture medium. Preferred salinity ranged from 0.1 to 3.5‰ by weight. All cultures were re-streaked on fresh media plates on a weekly basis to ensure viability. Finally, samples of each isolate were frozen at −80° C. in Zobel medium supplemented with 10% glycerol for long term storage.

Applicants randomly picked colonies of all plates with between 30 and 300 colony forming units/milliliter (cfu/ml). However, most plates had fewer than 100 cfu/ml. All isolates were Gram-stained and the bacilli were kept for further testing. The bacilli isolates were labeled 'BE' for brittlestar extract and numbered, starting with 12. All isolates were tested for growth at the following salinities: 1.25‰, 2.5‰, 5‰, 10‰, 15‰, and 20‰.

Antimicrobial Testing

Figure 2A:
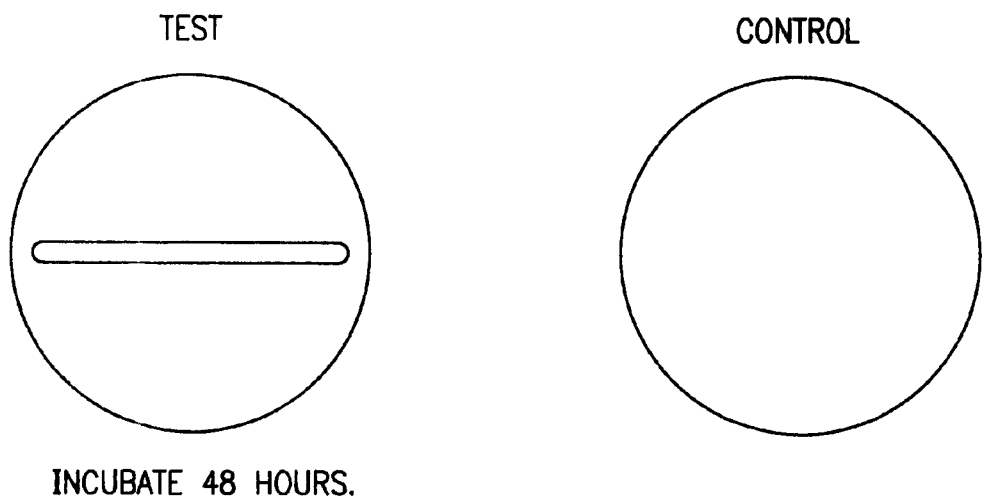
FIG. 2 schematically depicts the preferred method employed in rapid-streak testing of BE isolates for antimicrobial activity. (A) A BE isolate is streaked across the middle of a plate and incubated at 28° C. for 48 hrs. Control plates were streaked using a sterile applicator instead. (B) Several test bacteria are streaked perpendicular to the BE isolate streak, without touching each other or the BE streak. Plates are then incubated an additional 24 hours at 28° C. (35‰ salinity Zobel agar) or 37° C. (10‰ salinity Zobel agar), after which they are analyzed as described below.
Figure 2B:
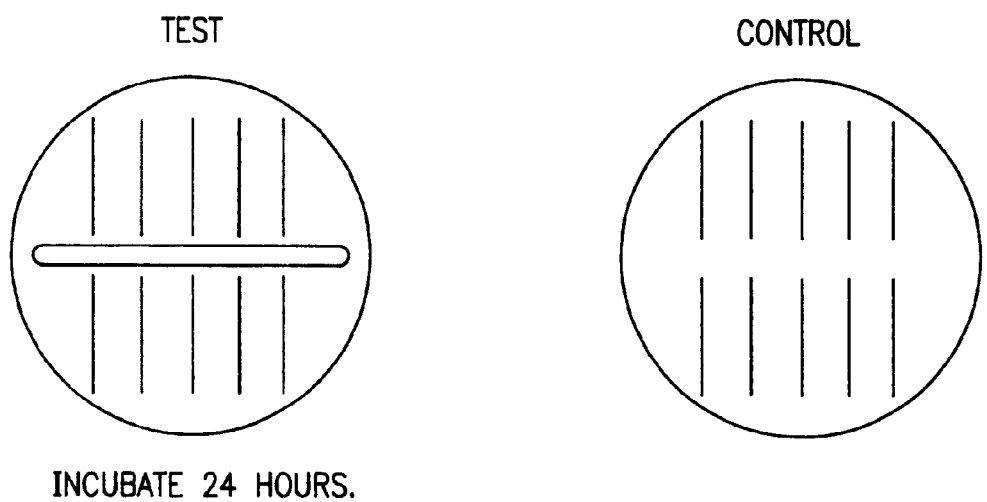

Sixteen (16) different species of bacteria (*Vibrio parahemolyticus, Klebsiella pneumoniae, Pseudomonas aeruginosa, Escherichia coli* K-12, *Salmonella typhimurium, Micrococcus luteus*, nontoxigenic *Corynebacterium diphtheriae, Enterobacter aerogenes, Mycobacterium smegmatis*, nontoxigenic *Staphylococcus aureus, Proteus vulgaris, Sporosarcina ureae, Bacillus subtilis, B. megaterium* and nontoxigenic *B. anthracis*) were used for rapid screening of antimicrobial activity by BE isolates. BE isolates were applied as a single streak on modified Zobel's medium (35‰ salinity), using aseptic technique (FIG. 2A). Plates were incubated at 28° C. for 48 hours. The test bacteria were then applied as single streaks perpendicular to the BE isolate streak, without touching it (FIG. 2B). The plates were incubated an additional 24 hours at 28° C. A zone of inhibition was defined as an area on the test streak of reduced growth or lack of growth. Partial inhibition was defined as significantly reduced growth over 10–20% of the streak. Lack of growth over 20–80% of the streak was defined as moderate inhibition. If the test organism did not grow, complete inhibition was scored. FIG. 3 presents Table 1, which illustrates these three classifications of inhibition zones, as well as areas where no inhibition occurred.

Figure 1:
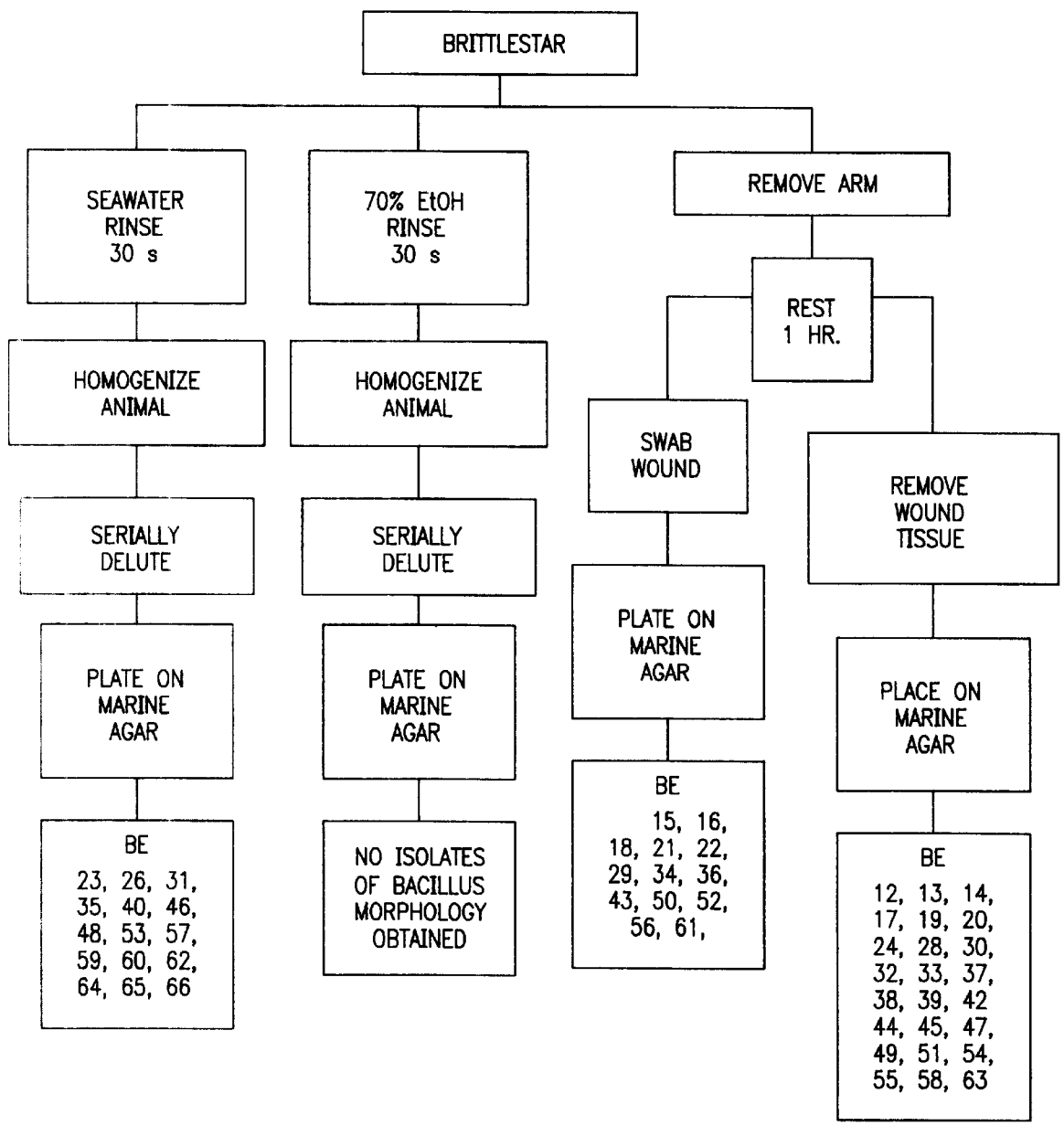
FIG. 1 is a flow chart depicting the four regimens utilized to isolate all bacilli used in this study. Using regimen 1, 15 bacilli were cultured. In regimen 2, only cocci were isolated. Regimen 3 produced 14 bacilli isolates, and 24 bacilli isolates were cultured in regimen 4. The numbers in the boxes at the bottom of each column indicate which bacterial isolates were cultured by each regimen.

FIG. 1 shows which isolates were recovered from the various isolation regimens. In all, fifty-nine cultures of bacilli were isolated. Of these, 25% were Gram positive and 75% were Gram negative. Cocci cultures were stored. Twelve percent of all isolates grew at 1.25‰ salinity and 95% of all isolates grew well at 2.5‰, 5‰, 10‰, 15‰ and 20‰ salinity. Table 1 shows individual inhibition exhibited by each isolate at both 35‰ and 10‰. Tests were performed at 35‰ salinity test because 35‰ is the salinity of the brittlestar's natural environment. Brittlestars are osmoconformers, so their body tissues are at the ambient salinity of their marine environment, which is about 35‰.

As depicted in Table 2, which follows, more BE isolates completely inhibited the test bacteria at 35‰ salinity than at 10‰ salinity. It is noted that *P. aeruginosa* was never completely inhibited.

TABLE 2

Percentage of All BE Isolates Exhibiting Complete Inhibition of Microbial Growth at Selected Salinities

| | Percentage of BE Isolates Completely Inhibiting Test Bacteria At: | |
|---|---|---|
| Test Bacterial Species | 35‰ | 10‰ |
| P. vulgaris | 17% | 1.7% |
| B. anthracis | 14% | 0% |
| B. catarrhalis | 6% | 0% |
| E. coli K-12 | 5% | 0% |
| M. smegmatis | 8.6% | 3.4% |
| S. ureae | 6.9% | 1.7% |
| S. typhimurium | 5.1% | 0% |
| S. aureus | 5.1% | 0% |
| C. diphtheriae | 5% | 0% |
| B. subtilis | 3.4% | 0% |
| E. aerogenes | 1.7% | 0% |
| K. pneumoniae | 1.7% | 0% |
| P. aeruginosa | 0% | 0% |

As depicted in Table 3, which follows, more BE isolates moderately inhibited the test bacteria at 35‰ salinity than at 10‰ salinity. The only exception was *P. aeruginosa*, which was moderately inhibited by more BE isolates at at 10‰ salinity than at 35‰ salinity.

TABLE 3

Percentage of All BE Isolates Exhibiting Moderate Inhibition of Microbial Growth at Selected Salinities

| | Percentage of BE Isolates Moderately Inhibiting Test Bacteria At: | |
|---|---|---|
| Test Bacterial Species | 35‰ | 10‰ |
| P. vulgaris | 70% | 16% |
| C. diphtheriae | 65% | 3.4% |

TABLE 3-continued

Percentage of All BE Isolates Exhibiting
Moderate Inhibition of Microbial Growth at Selected Salinities

| Test Bacterial Species | Percentage of BE Isolates Moderately Inhibiting Test Bacteria At: | |
|---|---|---|
| | 35‰ | 10‰ |
| B. catarrhalis | 60% | 6.9% |
| E. coli K-12 | 55% | 8.6% |
| S. typhimurium | 41% | 14% |
| B. anthracis | 47% | 14% |
| S. ureae | 40% | 22% |
| M. luteus | 40% | 8% |
| B. subtilis | 37% | 14% |
| K. pneumoniae | 37% | 1.7% |
| S. aureus | 34% | 6.9% |
| M. smegmatis | 28% | 1.7% |
| E. aerogenes | 14% | 3% |
| P. aeruginosa | 5.2% | 57% |

As presented in Table 4, which follows, fewer BE isolates, with the exception of three, partially inhibited the test bacteria at 35‰ salinity, when compared to 10‰ salinity.

TABLE 4

Percentage of All BE Isolates Exhibiting
Partial Inhibition of Microbial Growth at Selected Salinities

| Test Bacterial Species | Percentage of BE Isolates Partially Inhibiting Test Bacteria At: | |
|---|---|---|
| | 35‰ | 10‰ |
| B. subtilis | 19% | 16% |
| K. pneumoniae | 10% | 6.9% |
| E. aerogenes | 7% | 5% |
| C. diphtheriae | 17% | 24% |
| S. ureae | 16% | 22% |
| P. aeruginosa | 14% | 59% |
| S. aureus | 12% | 36% |
| E. coli k-12 | 6% | 34% |
| M. luteus | 8.6% | 19% |
| B. anthracis | 3.4% | 28% |
| M. smegmatis | 3.4% | 38% |
| P. vulgaris | 1.7% | 31% |
| B. catarrhalis | 15% | 47% |
| S. typhimurium | 15% | 26% |

Antimicrobial Testing at Physiological Conditions

All BE isolates also were tested for antimicrobial activity at human blood salinity using modified Zobel's media at 0.9–1.0% (~10‰) salinity and at human body temperature. Rapid screening was repeated on all BE isolates using the following test bacteria: nontoxigenic *Corynebacterium diphtheriae, Sporosarcina ureae, Bacillus subtilis*, nontoxigenic *B. anthracis, Escherichia coli* K-12, *Serratia marcescens*, nontoxigenic *Staphylococcus aureus, Proteus vulgaris, Klebsiella pneumoniae, Enterobacter aerogenes, Streptococcus mutans, Salmonella typhimurium, Enterococcus faecalis, Pseudomonas fluorescens, P. aeruginosa, Micrococcus luteus, Yersinia enterocolitica*, and *Mycobacterium smegmatis*. The tests were run as above, except the incubation temperature was 37° C. The results of these tests are presented in Table 1 in the shaded areas. 'A' represents complete inhibition produced by the BE isolate; 'B' represents moderate inhibition; and 'C' means partial inhibition. 'nd' indicates that the particular test bacterium was not tested at that salinity. Blank cells represent no inhibition or very slight inhibition. A description of inhibition levels is presented above. Note that *B. megaterium* was not tested at 10‰ due to procedural flaws.

Discussion of Experiments and Results

All isolation regimens, except the 30 second ethanol dip, resulted in cultures of bacilli. Since the cuticle of *A. gracillima* is permeable to seawater, it is believed that the ethanol dip not only killed the host but all bacilli as well. Moreover, since previous studies indicated that brittlestar SCB are bacilli in morphology (McKenzie and Kelly 1994), applicant only utilized the bacilli-shaped bacteria for testing in this study. Although SCB have been reported as being Gram-negative by observation under TEM, Gram-positive isolates were also tested for antimicrobial activity.

As described above, all isolates exhibited antimicrobial activity of varying degrees at both 35‰ and 10‰ salinity. Only three types of inhibition were scored on both the 35‰ and 10‰ sensitivity test plates; complete, moderate and partial. (Table 1 as presented in FIG. 3.) All test bacteria were tested for sodium tolerance on 35‰ media. Of all test bacterial cultures available, only the sixteen mentioned above for the 35‰ tests appeared to be tolerant of high sodium concentration. Since there was a high level of complete and moderate inhibition exhibited on the 35‰ media compared to the 10‰ media, a 3.5% sodium concentration is considered the optimal salinity for all isolates recovered. Although the test organisms grew under these high salinity conditions, it is likely that this is a stressful environment for them.

All complete and moderate inhibitions indicate that the isolate bacteria are able to produce a water-soluble compound that prevents or completely inhibits the growth of other bacterial cultures. It is suggested that these compounds are water-soluble since the inhibition seems to spread throughout the plate. Therefore, complete and moderate inhibition, as exhibited, are believed to be due to a compound produced by the SCB. But, partial inhibitions that were exhibited may be due to the stress of growing at a suboptimal salinity.

Five more known organisms were tested against the isolates at 10‰ since it was of a lower sodium content. These were *Serratia marcescens, Enterococcus faecalis, Streptococcus mutans, Pseudomonas fluorescens*, and *Yersinia enterolitica. Vibrio parahemolyticus* was unable to grow on the 10‰ salinity agar Zobel plates. (However, applicant has grown *V. parahemolyticus* on Mueller-Hinton agar containing 10‰ NaCl; therefore; applicant suspects a lack of nutrients as the cause for its failure to grow on Zobel's Medium, rather than salinity.) Since the optimal salinity for the isolates is believed to be 35‰, since they are isolated from a marine source, the isolates themselves may have been under stress in the low salinity conditions. Isolates numbers 12 and 14 did not grow at 10‰ salinity, and number 13 did not grow well at 10‰ salinity. The possibility remains that the other isolates exhibit lower antimicrobial activity at 10‰ salinity. However, since a high percentage of BE isolates grew at 2.5%, they obviously have a high tolerance to changes in salinity, which one would expect from an estuarine organism.

The following examples are set forth to illustrate the subject invention. Particularly, the following examples describe the BE isolates found to have more preferable antimicrobial characteristics, exhibiting antimicrobial effects against all tested microbes. More particularly, the following examples exhibited antimicrobial effects against all tested microbes at human physiological pH. Additionally, the microorganisms described in the following examples represent novel species or strains of the genus Vibrio, in that the following biochemical test results correspond to test results expected from the genus Vibrio. Tables of standard test results for types of microorganisms are well known in the art, see e.g. *Bergy's Manual of Systematic Bacteriology*. The examples should not be considered as limiting, the scope of the invention being defined by the claims appended hereto.

FIG. 4 depicts gel electrophoresis displaying Hae III (Promega, 2800 Woods Hollow Road, Madison, Wis. 53711) restriction fragment length polymorphism (RFLP) banding patterns of polymerase chain reaction (PCR)-amplified DNA from the 16S rRNA gene of isolates BE 37, BE 52, and BE 59. Standard molecular weight markers, 50 to 2000 basepair ladder, (BioRad Laboratories, 2000 Alfred Nobel Drive, Hercules, Calif. 94547) are also displayed. A standard restriction digest of the DNA was performed using the restriction enzyme Hae III according to well-known procedures and according to parameters recommended by the manufacturer of the restriction enzyme. Standard gel electrophoresis on a 12% polyacrylamide gel in 1×Tris-borate-EDTA (TBE) buffer, pH 8.0, was performed according to well-known techniques, such as those described in Sambrook et al. (1989).

Table 5 below sets forth the biochemical tests used to characterize all BE isolates.

TABLE 5

Biochemical Tests

Substrate Utilization

| Sugars & Alcohols Tested for | Amino Acids Tested for | Other Acids Tested for | Enzyme Activity Tested for |
|---|---|---|---|
| Galactose | Glutamate | Acetate | Catalase |
| Glucose | Glycine | Citrate | NO₃ Reductase |
| Lactose | | | |
| Maltose | | | |
| Mannose | | | |
| Rhamnose | | | |
| Ribose | | | |
| Sucrose | | | |
| Xylose | | | |
| Mannitol | | | |

Example 1 - Isolate Number BE 37 (ATCC202111)

Gram negative, short, slender, curved to straight bacilli.
Colony morphology: Irregular, uneven edge, flat, glistening, white and translucent.
Nitrate reductase negative.
Catalase positive.
Growth at 30° C., 37° C. & 40° C. No growth at 4° C.

| | Substrates Catabolized | | |
|---|---|---|---|
| Sugars/ Sugar Alcohols | Acid from Sugars Catabolized | Amino Acids Testing Positive | Other Organic Acids Testing Positive |
| Galactose | No | Glutamate | None |
| Glucose | Yes | | |
| Lactose | No | | |
| Maltose | Yes | | |
| Mannose | No | | |
| Rhamnose | No | | |
| Ribose | No | | |
| Sucrose | No | | |
| Xylose | No | | |
| Mannitol | No | | |

Example 2 - Isolate Number 59 (ATCC202112)

Gram negative, short, slender, curved, bacilli.
Colony Morphology: Irregular with uneven edge, flat, waxy, yellow and translucent
Nitrate reductase negative.
Catalase negative.
Growth at 30° C., 37° C. & 40° C. No growth at 4° C.

| | Substrates Catabolized | | |
|---|---|---|---|
| Sugars/ Sugar Alcohols | Acid from Sugars Catabolized | Amino Acids Testing Positive | Other Organic Acids Testing Positive |
| Galactose | No | None | Citrate |
| Glucose | Yes | | |
| Lactose | Yes | | |
| Maltose | No | | |
| Rhamnose | Yes | | |
| Mannitol | Yes | | |
| Xylose | Yes | | |

Example 3 - Isolate Number BE 52 (ATCC202113)

Gram negative, slender, short, curved to straight bacilli.
Colony Morphology: Circular with even edge, flat, rough, white, and translucent.
Nitrate reductase negative.
Catalase negative.
Growth at 30° C., 37° C. & 40° C. No growth at 4° C.

| | Substrates Catabolized | | |
|---|---|---|---|
| Sugars/ Sugar Alcohols | Acid from Sugars Catabolized | Amino Acids Testing Positive | Other Organic Acids Testing Positive |
| Galactose | No | None | None |
| Lactose | No | | |
| Maltose | Yes | | |
| Rhamnose | No | | |
| Mannitol | No | | |

REFERENCES

The references listed below as well as all references cited in the specification are incorporated herein by reference to the extent that they supplement, explain, provide a background for or teach methodology, techniques and/or compositions employed herein.

*Bergy's Manual of Systematic Bacteriology*, (Krieg, N. R., ed., Holt, J. R. ed.-in-chief), Williams and Wilkins, Baltimore, Vol. 1–4 (1984).

Bryan et al. (1994) 17–23 IN: David, B., A. Guille, J. Feral, & M. Roux (eds). *Echinoderms Through Time*, Balkema, Rotterdam.

Dobson, W. E. (1988) Early post-autonomy tissue regeneration and nutrient translocation in the brittlestar *Microphiopholis gracillima* (Stimpson) (Echinodermata: Ophiuroidea) Unpublished Ph.D. thesis. University of South Carolina, Columbia.

Holland and Nealson. (1978) *Acta Zoological* 59: 169–185.

Kelly, M. S. & D. J. McKenzie. (1992) 225–228 IN: Scalera-liaci, L., C. Canicatti (eds). *Echinoderm Research 1991*, Balkema, Rotterdam.

Kelly, M. S. & D. J. McKenzie. (1995) *Marine Biology* 123: 741–756.

Lubchenco et al. (1994) *Ecology* 72: 371–412.

McKenzie, J. D. & Kelly, M. S. (1994) *Marine Biology* 120: 65–80.

Sambrook et al. (1989) *Molecular Cloning: A Laboratory Manual* (Cold Spring Harbor Laboratory Press, Cold Spring Harbor, N.Y.).

U.S. Pat. No. 4,247,542
U.S. Pat. No. 4,692,333
U.S. Pat. No. 4,694,069
U.S. Pat. No. 5,061,495
U.S. Pat. No. 5,344,647
U.S. Pat. No. 5,364,623
U.S. Pat. No. 5,470,827
U.S. Pat. No. 5,614,188
U.S. Pat. No. 5,695,552

Zobel, C. E. (1941) *Journal of Marine Research* 4: 42–75.

It will be understood that various details of the invention may be changed without departing from the scope of the invention. Furthermore, the foregoing description is for the purpose of illustration only, and not for the purpose of limitation—the invention being defined by the claims.

What is claimed is:

1. A biologically pure culture of a bacterial strain selected from the group consisting of ATCC 202111(BE 37), ATCC 202112(BE 59), ATCC 202113(BE 52) and a mutant thereof.

2. The biologically pure culture of claim 1, which is ATCC 202111 (BE 37), or a mutant thereof.

3. The biologically pure culture of claim 1, which in ATCC 202112 (BE 59), or a mutant thereof.

4. The biologically pure culture of claim 1, which is ATCC 202113 (BE 52), or a mutant thereof.

5. The culture of claim 1, wherein said culture is capable of producing an antimicrobial composition in a recoverable amount upon fermentation in an aqueous nutrient medium.

6. The culture of claim 1, wherein said culture is in a form suitable for use in control of microbial infection or microbial contamination.

7. An antimicrobial composition comprising the biologically pure culture of claim 1, wherein said composition is derived from said culture and has the antimicrobial activity of said culture.

8. A biologically pure culture of a bacterial strain having all of the identifying characteristics of ATCC 202111 (BE 37), ATCC 202112 (BE 59) or ATCC 202113 (BE 52).

* * * * *

UNITED STATES PATENT AND TRADEMARK OFFICE
CERTIFICATE OF CORRECTION

PATENT NO. : 6,210,947 B1  
DATED : April 3, 2001  
INVENTOR(S) : William E. Dobson Page 1 of 1

It is certified that error appears in the above-identified patent and that said Letters Patent is hereby corrected as shown below:

<u>Title page,</u>
Item [73], Assignee, replace "Appalachain" with -- Appalachian --.

Signed and Sealed this

Fifth Day of February, 2002

Attest:

Attesting Officer

JAMES E. ROGAN
*Director of the United States Patent and Trademark Office*